United States Patent
Bloom et al.

(10) Patent No.: US 11,197,709 B2
(45) Date of Patent: Dec. 14, 2021

(54) ELECTROSURGICAL SYSTEM

(71) Applicant: Medtronic Advanced Energy LLC, Minneapolis, MN (US)

(72) Inventors: Eliot Bloom, Minneapolis, MN (US); Jesse Smith, Minneapolis, MN (US); Michael Leners, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 640 days.

(21) Appl. No.: 15/841,672

(22) Filed: Dec. 14, 2017

(65) Prior Publication Data

US 2018/0256240 A1 Sep. 13, 2018

Related U.S. Application Data

(60) Provisional application No. 62/470,513, filed on Mar. 13, 2017.

(51) Int. Cl.
  *A61B 18/12* (2006.01)
  *A61B 18/14* (2006.01)
  *A61B 18/00* (2006.01)

(52) U.S. Cl.
  CPC ...... *A61B 18/1206* (2013.01); *A61B 18/1445* (2013.01); *A61B 18/1482* (2013.01);
  (Continued)

(58) Field of Classification Search
  CPC ............ A61B 18/1206; A61B 18/1445; A61B 18/1482; A61B 18/1492; A61B 2018/0016; A61B 2018/00238; A61B 2018/00625; A61B 2018/00654; A61B 2018/00684; A61B 2018/00702; A61B 2018/00726; A61B 2018/00738; A61B 2018/00791;
  (Continued)

(56) References Cited

U.S. PATENT DOCUMENTS

| 4,195,637 A | 4/1980 | Gruntzig et al. |
| 4,492,231 A * | 1/1985 | Auth ..................... A61B 17/30 606/40 |

(Continued)

FOREIGN PATENT DOCUMENTS

| CN | 203354639 | 12/2013 |
| EP | 0966920 B1 | 4/2004 |

(Continued)

*Primary Examiner* — Daniel W Fowler
(74) *Attorney, Agent, or Firm* — Dicke, Billig & Czaja, PLLC

(57) ABSTRACT

An electrosurgical system includes a radiofrequency (RF) generator having a controller configured to detect an occurrence of a vaporization point of target tissue and a vaporization duration between commencement of delivery of the RF energy and the occurrence of the vaporization point. The controller can apply the vaporization duration to adjust a parameter during subsequent electrode activation, such as RF power level, an electrode activation sequence, a distance between activated electrodes, and a number of activated electrodes. The controller can apply the vaporization duration to determine if whether a predetermined depth of effect has been reached for use in subsequent parameter adjustments.

36 Claims, 9 Drawing Sheets

(52) U.S. Cl.
CPC .. *A61B 18/1492* (2013.01); *A61B 2018/0016* (2013.01); *A61B 2018/00238* (2013.01); *A61B 2018/00625* (2013.01); *A61B 2018/00654* (2013.01); *A61B 2018/00684* (2013.01); *A61B 2018/00702* (2013.01); *A61B 2018/00726* (2013.01); *A61B 2018/00738* (2013.01); *A61B 2018/00791* (2013.01); *A61B 2018/00875* (2013.01); *A61B 2018/00892* (2013.01); *A61B 2018/124* (2013.01)

(58) Field of Classification Search
CPC  A61B 2018/00875; A61B 2018/00892; A61B 2018/124
See application file for complete search history.

(56) References Cited

U.S. PATENT DOCUMENTS

| | | | | |
|---|---|---|---|---|
| 5,472,443 | A | * | 12/1995 | Cordis ............... A61B 18/1206 606/48 |
| 5,769,880 | A | | 6/1998 | Truckai et al. |
| 5,797,903 | A | | 8/1998 | Swanson et al. |
| 5,971,980 | A | * | 10/1999 | Sherman .......... A61B 17/22012 606/34 |
| 6,050,994 | A | * | 4/2000 | Sherman ............ A61B 18/1492 606/42 |
| 6,216,704 | B1 | | 4/2001 | Ingle et al. |
| 6,398,779 | B1 | * | 6/2002 | Buysse ............. A61B 18/1445 606/34 |
| 7,303,531 | B2 | | 12/2007 | Lee et al. |
| 7,615,013 | B2 | | 11/2009 | Clifford et al. |
| 7,635,340 | B2 | | 12/2009 | Vetter et al. |
| 7,993,337 | B2 | | 8/2011 | Lesh |
| 8,066,727 | B2 | | 11/2011 | Vetter et al. |
| 8,992,441 | B2 | | 3/2015 | Vetter et al. |
| 9,039,633 | B2 | | 5/2015 | Vetter et al. |
| 9,125,668 | B2 | | 9/2015 | Subramaniam et al. |
| 9,155,527 | B2 | | 10/2015 | Vetter et al. |
| 9,259,211 | B2 | | 2/2016 | Vetter et al. |
| 9,556,114 | B2 | | 1/2017 | Duggan et al. |
| 2002/0002372 | A1 | * | 1/2002 | Jahns ................ A61B 18/1492 606/41 |
| 2003/0055420 | A1 | * | 3/2003 | Kadhiresan ............ A61B 18/12 606/41 |
| 2003/0144653 | A1 | * | 7/2003 | Francischelli ..... A61B 18/1492 606/32 |
| 2003/0208123 | A1 | * | 11/2003 | Panescu ................ A61B 8/483 600/431 |
| 2005/0171583 | A1 | * | 8/2005 | Mosher ............. A61B 17/0625 607/96 |
| 2006/0229650 | A1 | | 10/2006 | Vetter et al. |
| 2009/0306659 | A1 | * | 12/2009 | Buysse ................. A61B 18/14 606/50 |
| 2010/0125188 | A1 | | 5/2010 | Schilling et al. |
| 2012/0035503 | A1 | | 2/2012 | Vetter et al. |
| 2013/0085493 | A1 | | 4/2013 | Bloom et al. |
| 2013/0226028 | A1 | | 8/2013 | Vetter et al. |
| 2013/0231571 | A1 | | 9/2013 | Lee et al. |
| 2014/0058197 | A1 | | 2/2014 | Salahieh et al. |
| 2014/0155779 | A1 | | 6/2014 | Vetter et al. |
| 2014/0357956 | A1 | * | 12/2014 | Salahieh ............ A61B 1/00082 600/160 |
| 2015/0045787 | A1 | | 2/2015 | Bloom |
| 2015/0057567 | A1 | | 2/2015 | Vetter et al. |
| 2015/0057569 | A1 | | 2/2015 | Vetter et al. |
| 2015/0057573 | A1 | | 2/2015 | Vetter et al. |
| 2016/0089208 | A1 | | 3/2016 | Vetter |
| 2016/0175041 | A1 | | 6/2016 | Govari et al. |
| 2016/0206340 | A1 | | 7/2016 | Vetter et al. |
| 2017/0055966 | A1 | | 3/2017 | Vetter et al. |
| 2017/0056040 | A1 | | 3/2017 | Vetter et al. |

FOREIGN PATENT DOCUMENTS

| | | |
|---|---|---|
| EP | 0983749 B1 | 5/2005 |
| EP | 3135237 | 1/2017 |
| WO | 2005039446 A1 | 5/2005 |
| WO | 2005060560 A2 | 7/2005 |
| WO | 2005067442 A2 | 7/2005 |
| WO | 2014105271 A1 | 7/2014 |
| WO | 2014172396 A2 | 10/2014 |
| WO | 2015026979 A2 | 2/2015 |
| WO | 2016053742 A1 | 4/2016 |
| WO | 2016138424 A1 | 9/2016 |
| WO | 2016141186 A1 | 9/2016 |
| WO | 2016141195 A1 | 9/2016 |
| WO | 2016144834 A1 | 9/2016 |

* cited by examiner

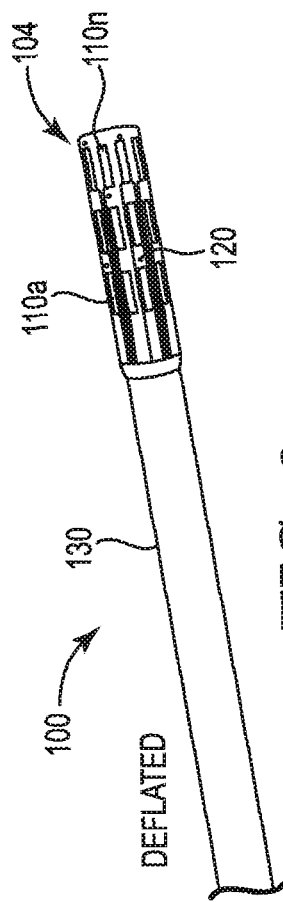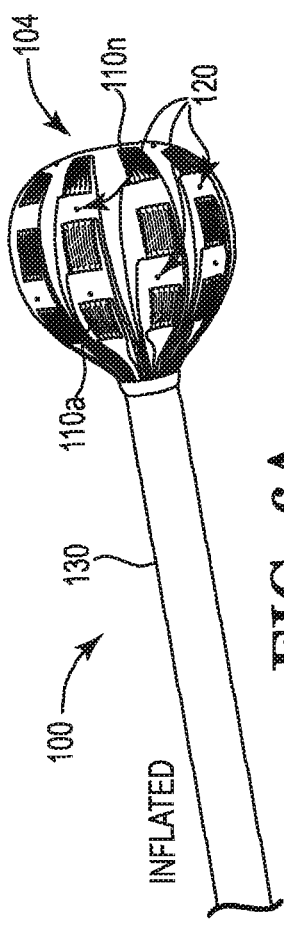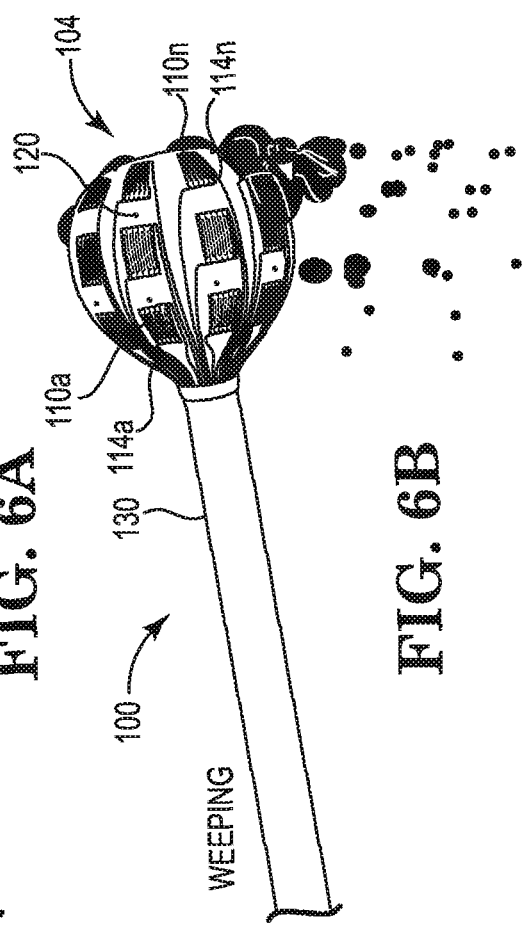

ELECTROSURGICAL SYSTEM

CROSS-REFERENCE TO RELATED APPLICATIONS

This Non-Provisional Utility Application claims benefit to U.S. Provisional Application No. 62/470,513, filed Mar. 13, 2017, titled "ELECTROSURGICAL SYSTEM," the entirety of which incorporated herein by reference.

BACKGROUND

The present disclosure relates generally to medical devices, systems, and method for use in surgical procedures. More specifically, the disclosure relates to electrosurgical systems with radiofrequency (RF) generator control based on a duration between commencement of delivery of RF energy and vaporization of the target tissue.

Electrosurgical systems employ RF energy to perform surgical procedures on target tissue, including cutting, ablation, coagulation, desiccation, resection, and/or sealing the target tissue. Such systems employ an RF generator to generate and control the RF energy. In one example, an effective procedure may endeavor to terminate energy delivery at the optimal time; namely, quickly enough to prevent unintended tissue damage, but not so quickly that the procedure is incomplete and ineffective. Various parameters and control schemes are used in order to precisely control the delivered RF energy in order to achieve the desired surgical result without unintended consequences such as charring of tissue or damage to tissue adjacent to the intended target tissue. As examples, RF generator controllers control the voltage, current, power, etc. of the delivered RF energy. To this end, measurements associated with the surgical site are made, such as tissue temperature and impedance, and the resulting signals are fed back to the RF generator controller.

The RF energy is delivered to the treatment site with an instrument, sometimes referred to as an electrosurgical device, tool, probe, or handpiece, including one or more bipolar or monopolar electrodes. Some electrosurgical instruments utilize an array of electrodes that are selectively energized and de-energized in order to optimize the delivery of RF energy to the target tissue. Various form factors for the electrosurgical tool are used depending on the intended surgical site. For example, some electrosurgical tools are provided in the form of balloon structures in which the electrodes are supported by an expandable structure to contact the target tissue. Depending on the application, saline is sometimes introduced to the treatment site in order to affect additional or alternative tissue heating through saline ionized by the RF energy.

SUMMARY

According to the disclosure, an electrosurgical system includes an electrosurgical device such as a catheter assembly, a plurality of electrodes supported by the catheter assembly and configured to deliver an RF signal to target tissue, and an electrosurgical generator such as an RF generator. The RF generator includes an impedance detector configured to generate impedance measurements indicative of an impedance associated with the target tissue, a controller, and an RF output stage configured to generate the RF signal in response to the controller. The controller is responsive to the impedance measurements from the impedance detector and configured to (a) detect an occurrence of a vaporization point of the target tissue, (b) detect a vaporization duration indicative of a time duration between commencement of delivery of the RF signal and the occurrence of the vaporization point, and (c) determine if a predetermined depth of effect has been reached based at least in part on the vaporization duration Features may include one or more of the following. The controller may be configured to detect the occurrence of the vaporization point of the target tissue by detecting an increase in the impedance measurements followed by a plateau in the impedance measurements. The system may include a depth of effect look up table containing a plurality of depth of effect values, each associated with a vaporization duration and a power level of the RF signal, wherein the look up table is used by the controller to determine if the predetermined depth of effect has been reached. Each of the plurality of depth of effect values may be further associated with at least one of a distance between activated electrodes and a surface area associated with the plurality of electrodes.

In some embodiments, the controller may be configured to adjust a power level for the RF signal if it is determined that the predetermined depth of effect has not been reached. The electrosurgical system may include a power look up table containing a plurality of power adjustment values, each associated with a vaporization duration, a power level of the RF signal, and a difference between a calculated depth of effect and a target depth of effect, wherein the power look up table is used by the controller to determine a new power level for the RF signal. Each of the power adjustment values in the power look up table may be further associated with at least one of a distance between activated electrodes and a surface area associated with the plurality of electrodes.

The plurality of electrodes may comprise a plurality of pairs of electrodes and the controller may be configured to activate the plurality of pairs of electrodes according to a sequence and to control the sequence of activations of the plurality of electrode pairs based on the vaporization duration. In some embodiments, the controller may be configured to control the sequence of activations of the plurality of electrode pairs by changing a distance between electrodes comprising the electrode pairs. In some embodiments, the controller may be configured to modify a number of activated electrodes if it is determined that the predetermined depth of effect has not been reached.

The impedance detector may be coupled to the plurality of electrodes and the impedance measurements may be indicative of the impedance between the electrodes. In some embodiments, the catheter assembly may comprise an inflatable balloon supporting the plurality of electrodes. The inflatable balloon may include a plurality of fluid delivery weeping holes.

In one aspect, the disclosure relates to an electrosurgical device having an elongate body and an expandable member. The elongate body includes a distal end and a proximal end, and a plurality of conductive signal lines. The expandable member is coupled to the distal end of the elongate body. The expandable member includes a non-conductive and expandable substrate having an outer surface and an inner surface to receive a fluid, the substrate having a deflated delivery configuration and an inflated expanded configuration. The expandable member also includes a plurality of electrode pairs attached to the outer surface of the substrate and electrically coupled to the conductive signal lines. Each electrode pair includes an active electrode spaced-apart on the substrate from a return electrode bipolar pair. The substrate includes a plurality of apertures on the outer surface disposed between the electrode pairs to expel the fluid in the expanded configuration.

In another aspect, the disclosure relates to an electrosurgical catheter assembly. The electrosurgical catheter assembly includes an elongate body having a distal end and a proximal end, the elongate body including a plurality of conductive signal lines, and an expandable member coupled to the distal end of the elongate body. The expandable member includes a non-conductive and expandable substrate having an outer surface and an inner surface to receive a fluid, the substrate having a deflated delivery configuration and an inflated expanded configuration. The expandable member also includes a plurality of electrode pairs attached to the outer surface of the substrate and electrically coupled to the conductive signal lines, wherein each electrode pair includes an active electrode spaced-apart on the substrate from a return electrode bipolar pair. In each of the electrode pairs the active electrode includes a plurality of spaced-apart active traces electrically in electrical communication, the return electrode includes a plurality of spaced-apart return traces, and the active traces are interleaved with the return traces.

In another aspect, the disclosure relates to a catheter assembly having an elongate body having a distal end and a proximal end, the elongate body including a plurality of conductive signal lines, and an expandable member coupled to the distal end of the elongate body. The expandable member includes a non-conductive and compliant substrate having an outer surface and an inner surface to receive a fluid, the substrate having a deflated delivery configuration and an inflated expanded configuration; and a plurality of electrode pairs attached to the outer surface of the substrate and electrically coupled to the conductive signal lines, wherein each electrode pair includes an active electrode spaced-apart on the substrate from a return electrode bipolar pair. The substrate includes a plurality of apertures on the outer surface and opened to expel the fluid in the expanded configuration and wherein the apertures are closed in the delivery configuration.

In still another aspect, the disclosure relates to an electrosurgical generator. The electrosurgical generator is couplable to a plurality of electrodes on an electrosurgical device to deliver a RF signal to a target tissue. The electrosurgical generator includes an impedance detector, a controller, and an RF output stage. The impedance detector generates impedance measurements indicative of an impedance associated with the target tissue. The controller is responsive to the impedance measurements from the impedance detector to detect an occurrence of a vaporization point of the target tissue, detect a vaporization duration indicative of a time duration between commencement of delivery of the RF signal and the occurrence of the vaporization point, and determine if a predetermined depth of effect has been reached based at least in part on the vaporization duration. The RF output stage generates the RF signal in response to the controller.

In another aspect, the disclosure relates to an electrosurgical generator. The electrosurgical generator is couplable to a plurality of electrodes on an electrosurgical device to deliver a RF signal to a target tissue. The electrosurgical generator includes an impedance detector, a controller, and an RF output stage. The impedance detector generates impedance measurements indicative of an impedance associated with the target tissue. The controller is responsive to the impedance measurements from the impedance detector to detect an occurrence of a vaporization point of the target tissue, detect a vaporization duration indicative of a time duration between commencement of delivery of the RF signal and the occurrence of the vaporization point, and adjust a parameter of the electrosurgical generator during a subsequent activation of an electrode of the plurality of electrodes based at least in part on the vaporization duration. The RF output stage generates the RF signal in response to the controller.

In still another aspect, the disclosure relates to a method for controlling an electrosurgical generator. The electrosurgical generator is couplable to a plurality of active electrodes on an electrosurgical device. For each of the plurality of electrodes in a succession of selected active electrodes, the method includes delivering an amount of radiofrequency (RF) energy to the selected active electrode to reach a vaporization point of tissue, and determining whether a depth of effect of tissue has reached a selected amount.

In still another aspect, the disclosure relates to an electrosurgical system including a catheter assembly, a plurality of electrodes supported by the catheter assembly and configured to deliver an RF signal to target tissue, and an RF generator. The RF generator includes an impedance detector configured to generate impedance measurements indicative of an impedance associated with the target tissue, a controller, and an RF output stage configured to generate the RF signal in response to the controller. The controller is responsive to the impedance measurements from the impedance detector and configured to (a) detect an occurrence of a vaporization point of the target tissue, (b) detect a vaporization duration indicative of a time duration between commencement of delivery of the RF signal and the occurrence of the vaporization point, and (c) adjust one or more parameters of the electrosurgical system during a subsequent activation of one or more of the plurality of electrodes based at least in part on the vaporization duration. The one or more parameters of the electrosurgical system may include one or more of: a power level of the RF signal, a sequence of activation of the plurality of electrodes, a distance between activated ones of the plurality of electrodes, and a number of activated electrodes.

In still another aspect, the disclosure relates to a method for controlling an electrosurgical generator. The electrosurgical generator is couplable to an electrosurgical device having an electrode in contact with a target tissue. The method includes applying an RF signal to an electrode in contact with a target tissue, measuring an impedance associated with the target tissue, analyzing the impedance measurements to determine if a vaporization point of the target tissue has occurred, determining a vaporization duration indicative of a time of application of the RF signal to the target tissue prior to the occurrence of the vaporization point, and analyzing the vaporization duration to determine if a predetermined depth of effect of the RF signal has been reached.

Features may include one or more of the following. Analyzing the impedance measurements may include detecting a plateau in the impedance measurements following a predetermined increase in the impedance measurements. Analyzing the vaporization duration to determine if a predetermined depth of effect of the RF signal has been reached may include using a depth of effect look up table containing a plurality of depth of effect values, each associated with a vaporization duration and a power level of the RF signal. The method may further include computing a new power level for the RF signal if it is determined that the predetermined depth of effect has not been reached. Computing the new power level may include using a power look up table containing a plurality of power adjustment values, each associated with a vaporization duration, a power level of the RF signal, and a difference between a calculated depth of effect and a target depth of effect. Applying an RF signal to an electrode may include applying the RF signal to a plurality of pairs of electrodes according to a sequence and wherein the method further comprises controlling the sequence based on the vaporization duration.

In still another aspect, the disclosure relates to a method for controlling an electrosurgical generator. The electrosurgical generator is couplable to an electrosurgical device having an electrode in contact with a target tissue. The method for controlling an electrosurgical system includes applying an RF signal to an electrode in contact with a target tissue, measuring an impedance associated with the target tissue, analyzing the impedance measurements to determine if a vaporization point of the target tissue has occurred, determining a vaporization duration indicative of a time of application of the RF signal to the target tissue prior to the occurrence of the vaporization point, and adjusting one or more parameters of the electrosurgical system during a subsequent application of the RF signal to an electrode in response to the vaporization duration.

Features may include one or more of the following. Adjusting one or more parameters may include adjusting a power level of the RF signal and/or modifying a number of activated electrodes. Applying the RF signal to an electrode may include applying, in a sequence, the RF signal to selected electrode pairs of a plurality of electrode pairs and adjusting one or more parameters may include adjusting the sequence of applying the RF signal to the electrode pairs. In some embodiments, adjusting the sequence of applying the RF signal to the electrode pairs may include changing a distance between electrodes of the electrode pairs.

BRIEF DESCRIPTION OF THE DRAWINGS

The foregoing features of the disclosure, as well as the disclosure itself may be more fully understood from the following detailed description of the drawings, in which like reference numbers refer to like elements and in which:

FIGS. 6, 6A, and 6B are perspective diagrams illustrating an example electrosurgical device of FIG. 1.

DESCRIPTION

Figure 1:
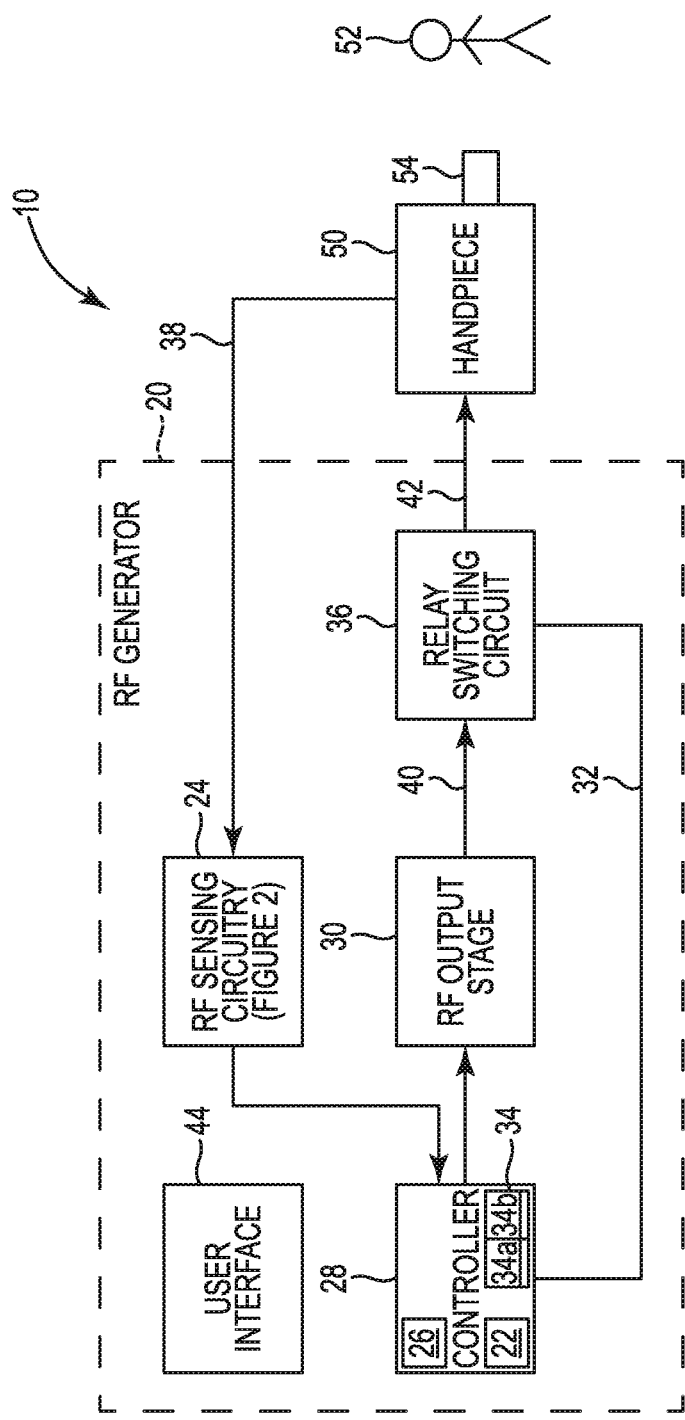
FIG. 1 is a block diagram illustrating an example electrosurgical system including an electrosurgical generator having an RF controller and an electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

Electrosurgery includes such techniques as cutting, coagulation, hemostasis, desiccation, resection, ablation, or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by a clinician, such as surgeon, and connected to the power source, such as an electrosurgical unit having a power generator, via cabling. Electrosurgical devices can be configured as catheter assemblies. For example, electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, the clinician could cut tissue using a first RF signal having a set of parameters to form plasma and control bleeding using a second RF signal having another set of parameters more preferred for coagulation. The clinician could also use electrodes in a bipolar arrangement or a bipolar electrosurgical device for hemostatic sealing of the tissue that would employ additional RF signals having another set of parameters.

Referring to FIG. 1, an electrosurgical system 10 includes electrosurgical generator such as an RF generator 20 configured to generate RF energy and an electrosurgical device having a handpiece 50 coupled to the RF generator and having electrodes 54 to receive and deliver RF energy to a patient treatment site, or target tissue 52 during an electrosurgical procedure. The RF generator 20 includes RF sensing circuitry 24, as may include an impedance detector, a controller 28 coupled to the RF sensing circuitry, and an RF output stage 30 to generate the RF signal 40 under control of the controller 28. A relay switching circuit 36 coupled between the RF output stage 30 and the handpiece 50 is configured to selectively energize and de-energize the electrodes 54 with an RF signal 42 in response to one or more control signals 32 from the controller 28.

The RF output stage 30 receives power from a power supply and generates RF signal 40 in the form of pulses and/or continuous waveforms, such as a sinusoidal waveform, for delivery to the electrodes 54. The controller 28 controls various parameters of the RF signal 40, such as power level, current level, voltage level, duty cycle, waveform type or shape, frequency, etc. The RF output stage 30 can be coupled to the RF sensing circuitry 24 to permit multiple paths for sensing signals in order to achieve redundancy and protect against single fault conditions.

Features of the RF generator 20 can include a display and a user interface 44 including user-actuatable controls with which the user can select certain treatment parameters. For example, the user may select a desired depth of penetration or effect of the RF energy into the target tissue (referred to herein as the depth of effect). Other user selectable parameters may include the RF voltage level, current level, power level, wave shape, and/or duty cycle.

Controller 28 may include, or be coupled to, memory 22, processor 26 (as may take the form of a microprocessor), and one or more look up tables (LUT) 34. The processor 26 is generally configured (e.g., programmed) to control operation of the RF generator 20 in response to user input(s) and adjustment settings and feedback signals 38. To this end, the processor 26 can be capable of executing software instructions for processing user inputs from user interface 44 and feedback signals 38 in order to achieve a desired surgical effect. Memory 22 can store software instructions and/or data, such as look up table data.

Figure 3:
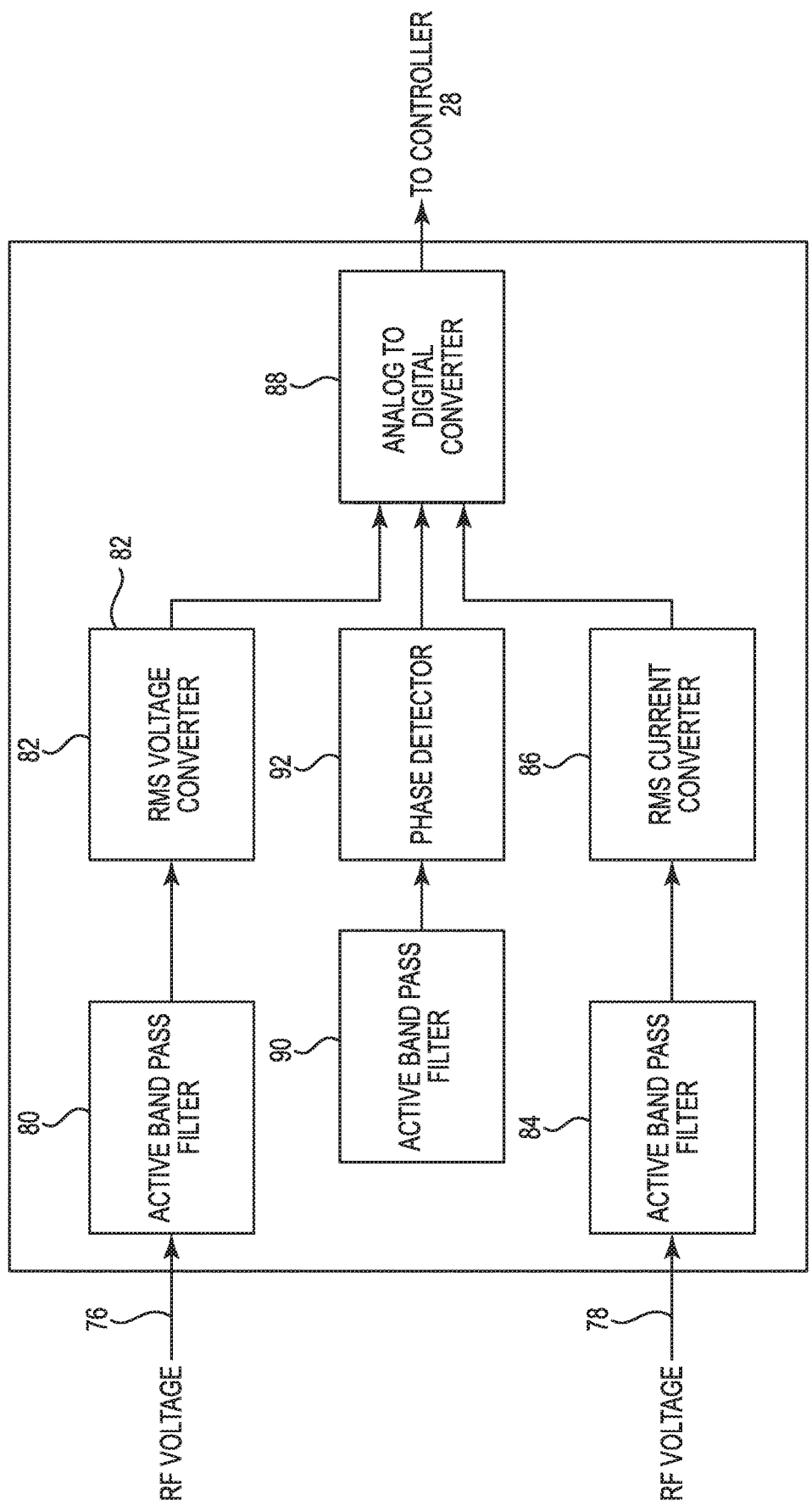
FIG. 3 is a schematic diagram illustrating a portion of the example electrosurgical generator of FIG. 1.

RF sensing circuitry 24 receives feedback signals 38 from electrodes 54 to generate impedance measurements indicative of an impedance associated with the target tissue 52. Example RF sensing circuitry 24 is shown in FIG. 3 and described below.

In operation, the controller 28 is responsive to the impedance measurements to detect an occurrence of vaporization of the target tissue 52 (referred to herein as the vaporization point) and to determine the time duration between commencement of delivery of RF energy to one or more selected electrodes and the occurrence of the vaporization point (referred to herein as the vaporization duration). Various schemes are possible for detecting the occurrence of vaporization, such as detecting a predefined increase followed by a plateau in the impedance of the target tissue as described below in connection with FIG. 4.

In one example, the look up tables 34 can include a depth effect look up table 34a and a power look up table 34b. In embodiments, the controller 28 is configured to determine if a predetermined depth of the target tissue has been affected by the applied RF energy (i.e., if a predetermined depth of effect has been achieved) based at least in part on the determined vaporization duration. For example, as described below, a depth of effect look up table 34a can be used by the controller to determine if the predetermined depth of effect has been reached. If it is determined that the predetermined depth of effect has not been achieved, the controller 28 may adjust the power level of the RF signal 40. In an embodiment, a power look up table 34b may be used by the controller to determine a new power level for the RF signal 40 again, as described below.

Furthermore, if it is determined that the predetermined depth of effect has not been achieved, the controller 28 may additionally or alternatively modify a sequence of electrode activation and/or change a number of activated electrodes. As will be explained, in some embodiments, modifying a sequence of electrode activation or a number of activated electrodes is an alternative to modifying the power level (see, e.g., FIG. 5A) and in other embodiments, modifying a sequence of electrode activation or a number of activated electrodes can be done after a new power level has been determined, but is not within a predetermined range (see, e.g., FIG. 5B). Furthermore, it will also be appreciated that if it is determined that the predetermined depth of effect has not been achieved, the controller 28 can adjust other parameters, such as duty cycle of the RF signal 40. Various schemes are possible to modify the sequence of electrode activation, including changing a distance between activated electrodes, such as by changing which electrodes form an electrode pair.

The controller 28 may use the determined vaporization duration to adjust one or more parameters of the electrosurgical system 10 during a subsequent activation of the electrodes 54. As examples, the vaporization duration can be used to adjust a power level of the RF signal 40 in order to ensure ideal depth of treatment, to control a sequence of energizing and de-energizing electrodes, and/or to control a distance between activated electrodes, and/or to change a number of activated electrodes.

The electrosurgical system and control apparatus and techniques described herein are suitable for performing various types of surgical procedures. By way of non-limiting examples, the electrosurgical system 10 may be used for cutting, ablation, coagulation, desiccation, resection, and/or sealing. Example applications include treatment of the pocket left behind after a lumpectomy, treatment of tissue to kill cancer cells in other areas such as Barrett's esophagus, ablation of tissue in support renal denervation, providing hemostasis for the treatment of ulcers located in the upper and lower track of the intestines, and modeling of cardiac tissue in support of better blood flow or seating within the valve.

In one treatment example, the pocket left behind after a lumpectomy is treated with cooled RF energy (RF energy without the use of external saline). Without the introduction of saline, it is possible to use the described techniques to sense the tissue to determine tissue depth. Following the initial treatment of the tissue, the procedure can continue with the application of RF energy with saline. With the introduction of saline as a conduit for the RF energy, it can be assured that all of the tissue that requires treatment is exposed to the RF energy.

Figure 2:
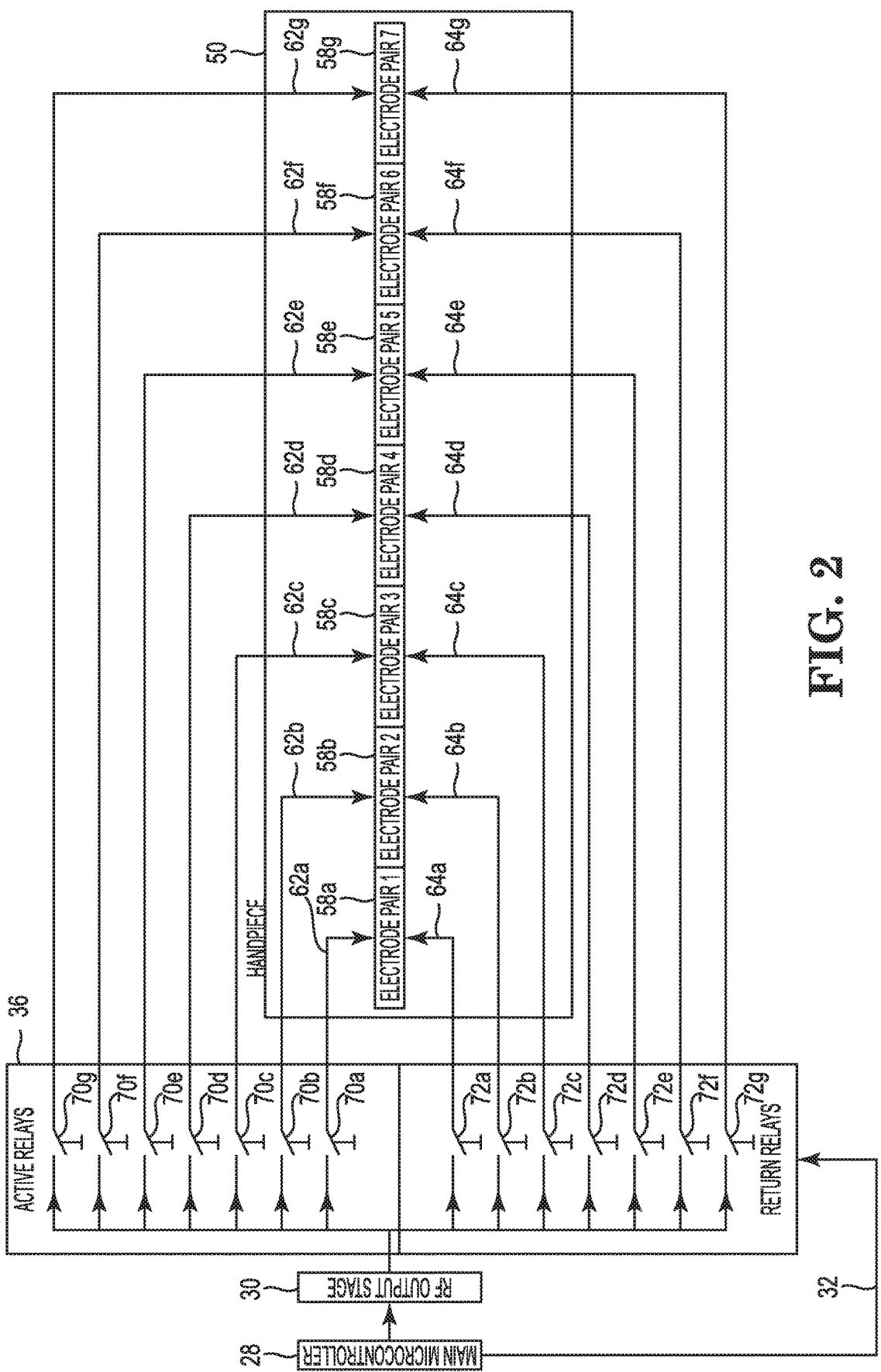
FIG. 2 is a schematic diagram illustrating an example of a portion of the system of FIG. 1.

Referring also to FIG. 2, a portion of the electrosurgical system 10 of FIG. 1 is shown to illustrate control of electrodes 54 of the handpiece 50. Various configurations and control schemes are suitable for electrodes 54. In general, a plurality of electrodes, or electrode pairs, or sets of electrodes, here represented by electrode pairs 58a-58g, are supported by a delivery structure, such as a catheter with a balloon (FIGS. 6, 6A, and 6B). Electrodes 54 are coupled to the relay switching circuit 36 by conductors or conductive traces 62a-62g, 64a-64g, as shown.

In some embodiments, the electrodes 54 are arranged in a plurality of bipolar pairs 58a-58g, with each pair including two electrodes and each electrode of the pair electrically coupled to the relay switching circuit 36 through a respective conductive trace. With this bipolar electrode arrangement, one electrode from each pair functions as the active electrode serving as a first pole of a bipolar electrode configuration to receive RF current from the RF output stage 30 for delivery to the target tissue and the other electrode of the pair functions as the return electrode serving as a second pole of the bipolar electrode configuration to return current to the RF output stage 30. To this end, each electrode pair 58a-58g is coupled to the relay switching circuit 36 by a respective active, or power trace 62a-62g and a respective return trace 64a-64g, as shown. The relay switching circuit 36 includes a plurality of active relays 70a-70g and a plurality of return relays 72a-72g. More particularly, relays 70a-70g can be considered active relays since, when closed, they couple the active electrode of the respective electrode pair to receive RF energy from an active terminal the RF output stage 30 and relays 72a-72g can be considered return relays since, when closed, they couple the return electrode of the respective electrode pair to a return terminal of the RF output stage 30, such as ground.

The relays 70a-70g, 72a-72g are controlled by control signals 32 from the controller 28 in order to enable selective and individual control of the electrodes 54. For example, the relays 70a-70g, 72a-72g can be controlled so as to activate each electrode pair 58a-58g in a desired sequence. The sequence can be sequential, for example, beginning with activation of electrode pair 58a and then, in order, activating pairs 58b through 58g. The sequence of electrode pair activation can be random or it can follow some other predefined order.

The sequence of electrode pair activations can be a predetermined sequence that is established before the medical procedure is initiated and that does not vary during the procedure. Alternatively however, the electrode activation sequence can be dynamically adjusted during operation in order to optimize the procedure. For example, the electrode activation sequence can be dynamically adjusted during operation based on the vaporization duration. It will be appreciated that there are many different ways to adjust the electrode activation sequence. For example, the electrode activation sequence can be varied simply by changing the order in which the electrode pairs 58a-58g are activated. For example, one sequence can have the pairs activated in the following order: 58a, 58b, 58c, 58d, 58e, 58f, and 58g; while a different sequence can have the pairs activated in the following order: 58a, 58c, 58e, 58g, 58b, 58d, 58f. The distance between electrodes forming a bipolar electrode pair can vary the RF application to the tissue. For example, the closer the bipolar electrodes are to each other, the more focused the RF energy that is applied to the area between the electrodes, permitting deeper penetration of the RF energy into the tissue. The electrodes that form an electrode pair can be adjacent to each other, antipodal to each other, or any intermediate distance from each other. The electrodes that form an electrode pair can be dynamically adjusted during operation based on the vaporization duration and/or based on the calculated depth of effect in order to thereby change the distance between activated electrodes to achieve a desired treatment effect. Adjusting which electrodes form each electrode pair can be considered another way of effectively changing the sequence of electrode activations. Because the relays 70a-70g, 72a-72g are individually controlled, it will be appreciated that the particular electrodes that form each electrode pair can be varied. For example, while a first electrode pair 58a is shown in FIG. 2 to be formed by an electrode coupled to active relay 70a and an electrode coupled to return relay 72a, this electrode pair could alternatively be formed by an electrode coupled to active relay 70a and an electrode coupled to return relay 70d for example. It will be appreciated that changing which electrodes form each electrode pair can result in a change in the distance between activated electrodes. In some embodiments, a single electrode pair 58a-58g is activated at any given time. However, in embodiments in which it is desirable to modify the number of activated electrodes, it will be appreciated that this modification can be as simple as selecting two electrode pairs for simultaneous activation rather than one pair, for example.

Referring to FIG. 3, a block diagram of RF sensing circuitry 24 of FIG. 1 includes an impedance detector to generate impedance measurements indicative of the impedance of the target tissue. Various circuitry and techniques are suitable to detect tissue impedance. The illustrated RF sensing circuitry 24 computes impedance by measuring the RF voltage 76 and the RF current 78 at the treatment site 52 and using RMS values of the measured RF voltage and current to compute tissue impedance using Ohm's law. To this end, the RF sensing circuitry 24 is responsive to feedback signal(s) 38 (FIG. 1) as may take the form of RF voltage signal 76 and RF current signal 78 from the handpiece 50.

Various circuitry and techniques can be implemented, either internal or external to the handpiece 50, in order to sense the voltage and current at the treatment site 52. In embodiments, the voltage and current at each of the electrodes 54 as the electrodes are selectively energized can be measured and fed back to the sensing circuitry 24 as voltage and current signals 76, 78. In this fashion, individual feedback from the activated treatment electrodes 54, or electrode pairs 58a-58g, can be provided. It will be appreciated however that, alternatively, dedicated electrodes adjacent to the treatment electrodes can be used for impedance measurement.

A voltage divider and voltage transformer can be coupled between electrodes 54 and the sensing circuitry 24 in order to reduce the amplitude of the sensed, delivered RF voltage 76 and to isolate the patient from the RF generator circuitry. Similarly, a current transformer can be used to sense the RF current at the treatment site, in order to thereby isolate the patient from the RF generator circuitry. It will be appreciated that the voltage divider and voltage and current transformers can be located in or adjacent to the handpiece 50 or alternatively can form part of the RF sensing circuitry 24.

RF sensing circuitry 24 includes a band pass filter 80 to filter the measured RF voltage signal 76 and an RMS voltage converter 82 to convert the filtered RF voltage to an RMS voltage value. A band pass filter 84 is provided to filter the measured RF current signal 78 and an RMS current converter 86 converts the filtered RF current to an RMS current value. The RMS voltage from voltage converter 82 and the RMS current from current converter 86 can be coupled to an analog-to-digital converter (ADC) 88 in order to digitize these measurements for use by the controller 28.

In some embodiments, it may be desirable to implement plasma detection in order to establish voltage boundary conditions. Excess voltage can induce plasma and plasma should be avoided since it can cause patient tissue char. To this end, a further active band pass filter 90 may be responsive to both the measured RF voltage signal 76 and to the measured RF current signal 78 to generate filtered signals for coupling to a phase detector 92. Since plasma can cause phase shift and changes the crest factor and frequency content of the RF signal, plasma can be sensed by the phase detector 92 and the RF voltage can be lowered as necessary to avoid plasma generation. In some embodiments, the active band pass filters 80, 84, and 90 may take the form of two-stage Salen key filters.

The controller 28 responds to the digitized impedance measurements from the ADC 88 to detect vaporization of the target tissue, detect the vaporization duration (i.e., the time duration between commencement of delivery of the RF signal and the occurrence of vaporization), and to determine if a predetermined depth of effect has been reached based at least in part on the vaporization duration, as will be explained.

It will be appreciated that although the RF sensing circuitry 24 is shown for processing voltage and current feedback signals 76, 78 to generate tissue impedance information, additional or alternative sensors and techniques can be used and respective signals fed back to the RF sensing circuitry for processing to detect tissue impedance and for other purposes. As an example, a temperature sensor at or near the electrodes 54 can be employed to generate temperature information for coupling to the RF sensing circuitry 24 and/or to the controller 28.

Figure 4:
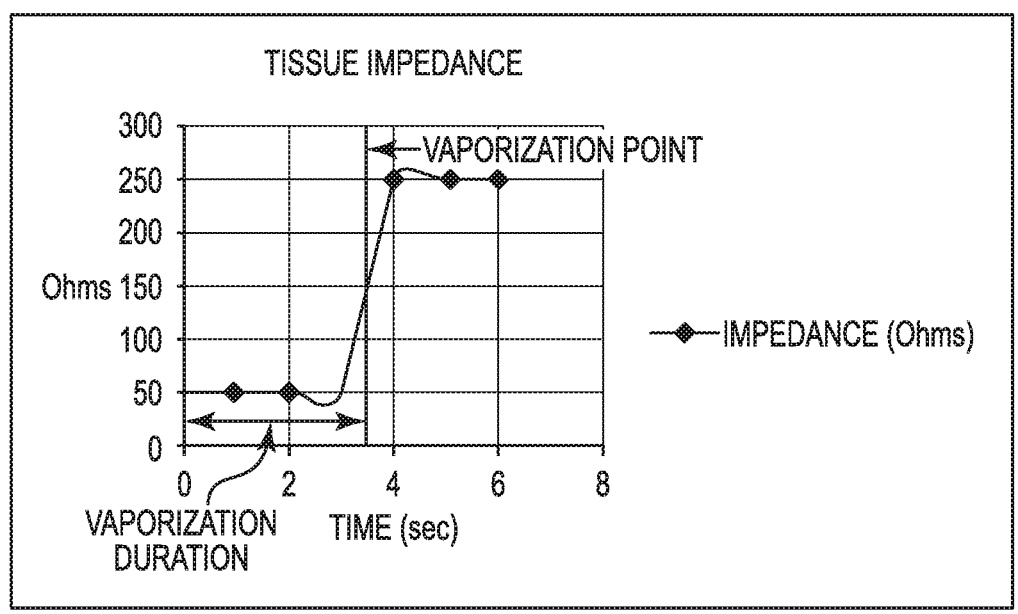
FIG. 4 illustrates an example impedance waveform.

Referring to FIG. 4, an example waveform illustrates impedance of target tissue 52 (FIG. 1) during delivery of RF energy to the tissue when saline is not being applied. The y-axis represents tissue impedance in units of ohms and the x-axis represents duration of RF energy delivery in units of seconds, with RF energy being delivered beginning at a time of zero seconds.

When tissue is treated with RF energy, there is a point at which vaporization of moisture in the tissue occurs. The point of vaporization generally coincides with an acute rise in impedance that is followed by a plateau. For example, the vaporization point is shown to occur at approximately 3.5 seconds in the example waveform. It will be appreciated that the specific impedances and times shown on the example waveform of FIG. 4 will vary depending on many factors such as the tissue type, RF power level, electrode form factor and configuration, etc.

Controller 28 detects the vaporization point by assessing changes in impedance measurements over time (i.e., by evaluating historical data in the form of stored impedance measurement samples). More particularly, the controller can detect the vaporization point by detecting the occurrence of an impedance plateau and then determining whether an acute rise, or increasing ramp preceded the plateau and if so, the time of occurrence of the ramp.

An impedance plateau, as shown to occur at approximately 5.0 seconds in the example waveform, can be defined to occur when a predetermined number of consecutive impedance samples have less than a predetermined amplitude difference between them. For example, the processor 26 may acquire a predetermined number of impedance measurement samples from the ADC 88. Once the predetermined number of impedance samples is stored, the processor may compute the change in impedance amongst the stored samples in order to determine if they have less than the predetermined amplitude difference between them.

Having determined that an impedance plateau has occurred, the processor 26 can determine whether vaporization has occurred by assessing a predetermined number of stored impedance samples prior to the plateau to detect a predetermined rise in the impedance values indicative of an acute ramp. Various conditions can be used to characterize a rise in impedance values as an acute increasing ramp. As one example, an acute ramp can be defined as occurring when a predetermined amplitude increase in one or more sequential impedance measurements occurs within a predetermined time interval.

The point at which tissue begins to vaporize generally coincides with a tissue temperature on the order of 100° C. and thus, the vaporization duration can be used as an indicator that the tissue temperature has reached 100° C. In some embodiments, it may be desirable to sequence to a new pair of electrodes when the vaporization point is detected in order to prevent the tissue temperature from exceeding 100° C.

The vaporization duration corresponds to the time duration between commencement of delivery of the RF energy (e.g., time 0 seconds in the example waveform) and the time at which the vaporization point occurs (e.g., time 3.5 seconds in the example waveform). If the acute ramp preceding the impedance plateau is detected, the vaporization duration can be provided by as indication of the time between commencement of the application of RF energy to the treatment site and occurrence of the acute ramp, as shown. Since the tissue impedance over time characteristics will vary based on factors including RF power level, tissue type/density, cavity temperature/humidity, electrode contact area, and distance between the electrodes, it will be appreciated that the processor 26 can be calibrated to use different sets of conditions to define and determine the occurrence of an impedance plateau and acute ramp in order to thereby determine the vaporization duration.

In accordance with control methodologies described herein, the detected vaporization duration during activation of selected electrodes can be used by the controller to determine if a predetermined depth of effect of the RF energy has been reached and system parameters, such as RF power, can be dynamically adjusted accordingly for use in subsequent electrode activations. Furthermore, the detected vaporization duration itself (even without calculation of the achieved depth of effect) can additionally or alternatively be used to dynamically adjust various parameters of the electrosurgical system for subsequent electrode activations, such as the RF power level, electrode sequencing and/or distance between energized electrodes and/or the number of activated electrodes. By analyzing the effects of RF energy applied during initial treatment without saline in this manner, system parameters used during subsequent electrode activations within that initial treatment and also during further treatment (such as with saline) can be optimized.

Figure 5:
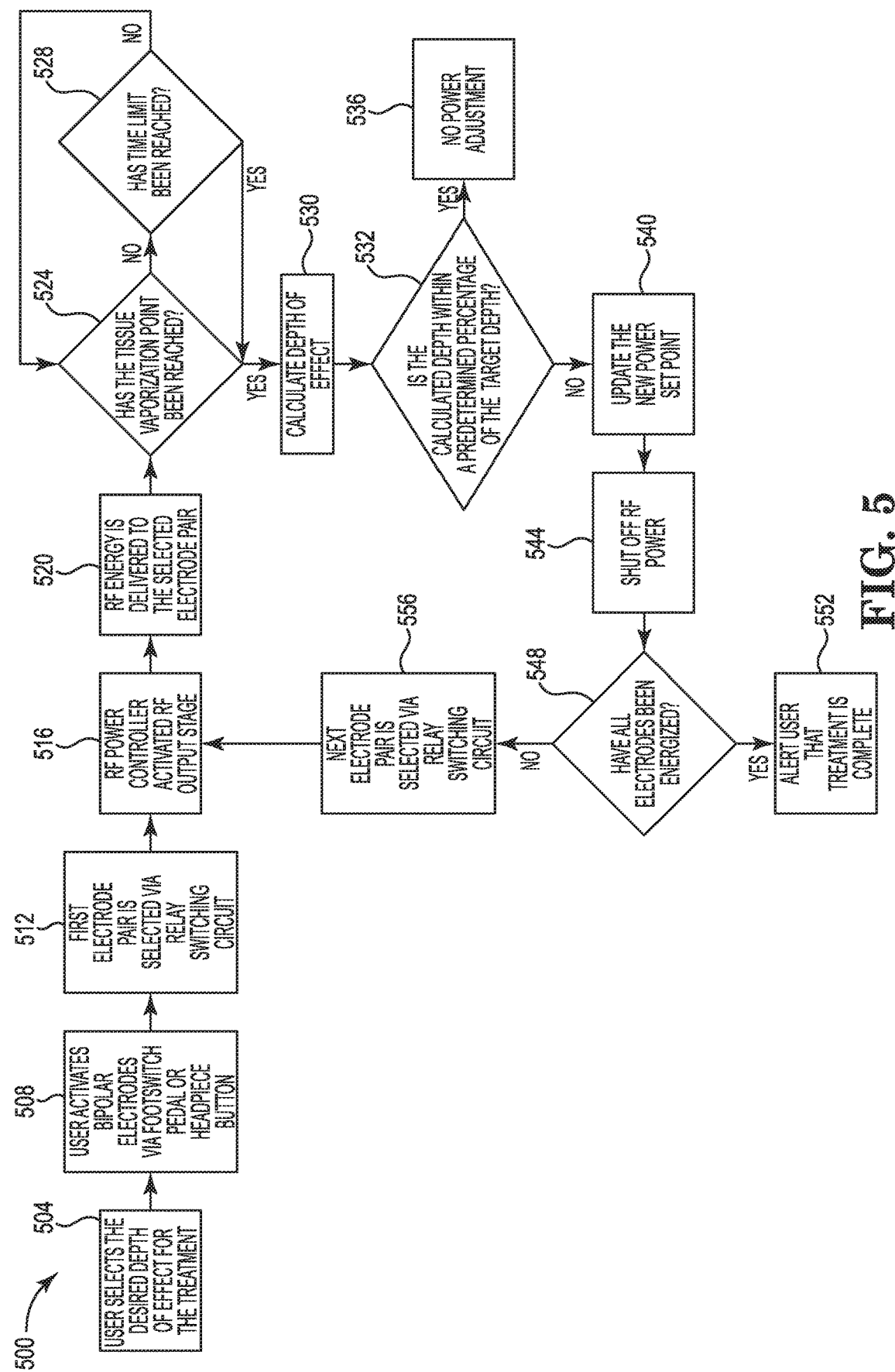
FIGS. 5, 5A, and 5B are flow diagrams illustrating a method of the example electrosurgical generator of FIG. 1.

Referring also to FIG. 5, a flow diagram illustrates a method 500 of operation of the electrosurgical controller 28. At block 504, a user selects a desired depth of effect for the treatment. This user selection may be made through the user interface 44 (FIG. 1) and may take the form of selection of depth of effect from a number of predefined choices, as may be presented in units of millimeters. In response to the user input, one or more initial system parameters are established, such as an RF power level. A depth of effect look up table 34*a* that is described in greater detail below can be used for this purpose.

At block 508, the user activates the bipolar electrodes, such as by actuating a footswitch pedal or handpiece button. At block 512, a first electrode pair is selected via the relay switching circuit 36. More particularly, the active and return relays coupled to the first electrode pair to be activated are closed. As noted above, which electrode pair (e.g., of pairs 58*a*-58*g* shown in FIG. 2) is the first pair (and subsequent pairs) to be energized can be established by a predetermined sequence of electrode pairs.

At block 516, the controller 28 is initialized and causes the RF output stage to generate the RF signal 40 according to the initial parameters determined based on the depth of effect selected by the user at block 504. At block 520, RF energy is delivered to the first selected electrode pair, without the introduction of saline.

At block 524, a determination is made as to whether vaporization has occurred. As explained above in connection with FIG. 4, the vaporization point can be determined by detecting whether a plateau in tissue impedance measurements following an acute ramp in the measured impedance values has occurred. To this end, block 524 may involve analysis of a predetermined number of stored tissue impedance measurement samples.

At block 528, it is determined whether a predetermined time limit has been reached since commencement of delivery of RF energy (i.e., at block 520). If the time limit has not yet been reached, then block 524 is again performed; whereas, once the time limit is reached, the depth of effect of the applied RF energy is calculated at block 530. The time limit of block 528 is used to prevent excessive treatment. If, within the predetermined time limit, vaporization has not occurred, then it is possible that the desired depth of effect has been achieved without having caused tissue vaporization.

Once the time limit has been reached at block 528 or it is determined at block 524 that tissue vaporization has occurred, the depth of effect of the applied RF energy is calculated at block 530. In an embodiment, a depth of effect look up table 34a (FIG. 1) may be used for this purpose.

The depth of effect look up table 34a may contain a plurality of values of depth of effect, such as in units of millimeters, with the table organized as a multi-dimensional array of parameters, or indexes, affecting the depth of effect, with each index having a value of between 0 and 10.00 for example. A first index (w) of the look up table may represent the activation time of the activated electrode pair, for example in 10 msec increments up to 20 seconds of activation time. A second index (x) of the look up table may represent the applied RF power, for example in 10 watt increments, up to 220 watts. A third index (y) of the depth of effect look up table may represent a distance between the two electrodes of the activated electrode pair, for example in 1 mm increments, up to 5 cm, and a fourth index (z) of the array may represent the electrode tissue contact surface area in $mm^2$.

Having calculated the depth of effect, at block 532, a determination is made as to whether the calculated depth is within a predetermined percentage of the desired, target depth as selected by the user at block 504. For example, it may be determined whether the calculated depth of effect is within approximately 20% of the desired target depth.

If it is determined in block 532 that the calculated depth of effect is within the predetermined percentage of the target depth, then in subsequent block 536, no RF power adjustment is made and the RF power is shut off in block 544, as shown. If however it is determined at block 532 that the desired depth of effect has not been achieved (e.g., the calculated depth of effect is not within 20% of the target depth of effect), then at block 540, a new power setting is determined for subsequent electrode activations, following which the RF power is shut off in block 544. In an embodiment, a power adjustment look up table 34b (FIG. 1) may be used for this purpose. Shutting off the RF power in block 544 protects the relays of the switching circuit 36 by avoiding RF power being delivered while the relays are switched. The off period may be very brief, such as on the order of 100-300 milliseconds.

The power look up table 34b may contain a plurality of values representing changes to the applied RF power in watts, with the table organized as a multi-dimensional array of parameters, or indexes, affecting the power change, with each index having a value of between 0 and 10.00 for example. A first index (v) of the power look up table may represent the activation time of the activated electrode pair, for example in 10 msec increments up to 20 seconds of activation time. A second index (w) of the look up table may represent the applied RF power for example in 10 watt increments, up to 220 watts. A third index (x) of the power look up table may represent a distance between the electrodes of the activated electrode pair, for example in 1 mm increments, up to 5 cm. A fourth index (y) of the power look up table may represent the electrode tissue contact surface area in $mm^2$ and a fifth index (z) may represent a delta depth of effect, as given by the depth set point (i.e., the depth of effect selected by the user at block 504) minus the calculated depth of effect, with that difference divided by the depth set point, and thereby provide a measure of how far off the achieved depth of effect is from the desired depth of effect. On the basis of the power look up table at block 540, the controller 28 adjusts the RF signal power accordingly.

At block 548, it is determined whether all of the electrodes 54 of the handpiece 50 have been energized. If all electrodes 54 have been energized, then at block 552, the user is alerted that the treatment is complete. It will be appreciated that block 552 may include providing additional information to the user, such as an indication that the desired depth of effect was or was not achieved during the procedure.

If however it is determined at block 548 that not all of the electrodes have been energized, then at block 556, the next electrode pair is selected by the relay switching circuit 36, following which the RF power controller in again initiated in block 516, as shown, but in this iteration with the RF signal having the updated power set point determined in block 540. In one example embodiment, the electrode pairs (e.g., pairs 58a-58g in FIG. 2) are sequentially selected. It will be appreciated however that other sequences of the plurality of electrode pairs are possible.

As noted above, the depth of effect look up table 34a can be used in block 504 to determine initial system parameters. For example, the initial power setting can be determined by solving for the (x) index using 5 seconds or some other preselected time as the treatment time.

Consideration of the flow diagram of FIG. 5 reveals a process by which the efficacy of RF energy applied during initial treatment without saline to reach a desired, target depth is assessed and used to alter (or not, based on the assessment) system parameters to achieve the desired target depth in subsequent electrode activations. Further treatment with or without saline may follow the procedure of FIG. 5 as deemed suitable.

It will be appreciated that while the flow diagram of FIG. 5 contemplates use of a plurality of selectively activated electrode pairs, in embodiments utilizing only a single electrode or electrode pair, blocks 548 and 556 may be eliminated. Furthermore, the method of FIG. 5 contemplates activation of each electrode pair in a sequence in succession, with each such activation followed by or otherwise associated with a determination of whether the tissue vaporization point has been reached (block 524). It will be appreciated that other arrangements are possible.

The above-described depth of effect and power look up tables 34a, 34b, respectively, can be populated based on empirical data collected by experimental application of a set of values for the indices and measurement of the resulting depth of effect for example. It will be appreciated that as an alternative or addition to the use of the above-described look up table determinations, other manners of computation may be used to calculate depth of effect and an updated power setting.

Figure 5A:
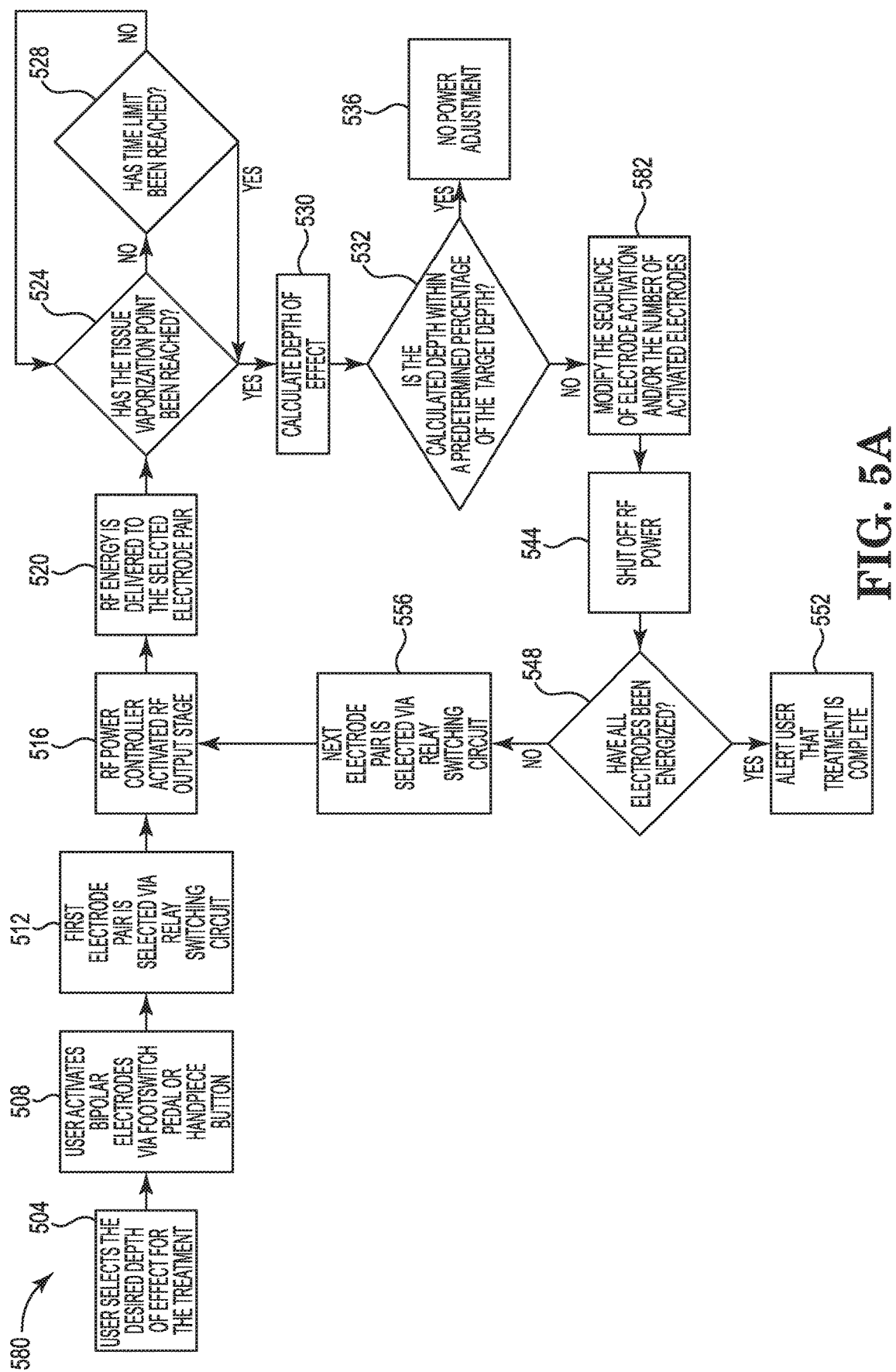

Referring also to FIG. 5A, a flow diagram illustrates an alternative method of operation 580 of the electrosurgical controller 28, in which like reference numbers with respect to FIG. 5 refer to like elements. In particular, FIG. 5A differs from FIG. 5 in that block 540 is replaced by block 582 to illustrate that modifying the sequence of electrode activation and/or the number of activated electrodes can be performed as an alternative to modifying the RF power level if it is determined in block 532 that the calculated depth of effect is not within the predetermined percentage of the target depth.

Figure 5B:
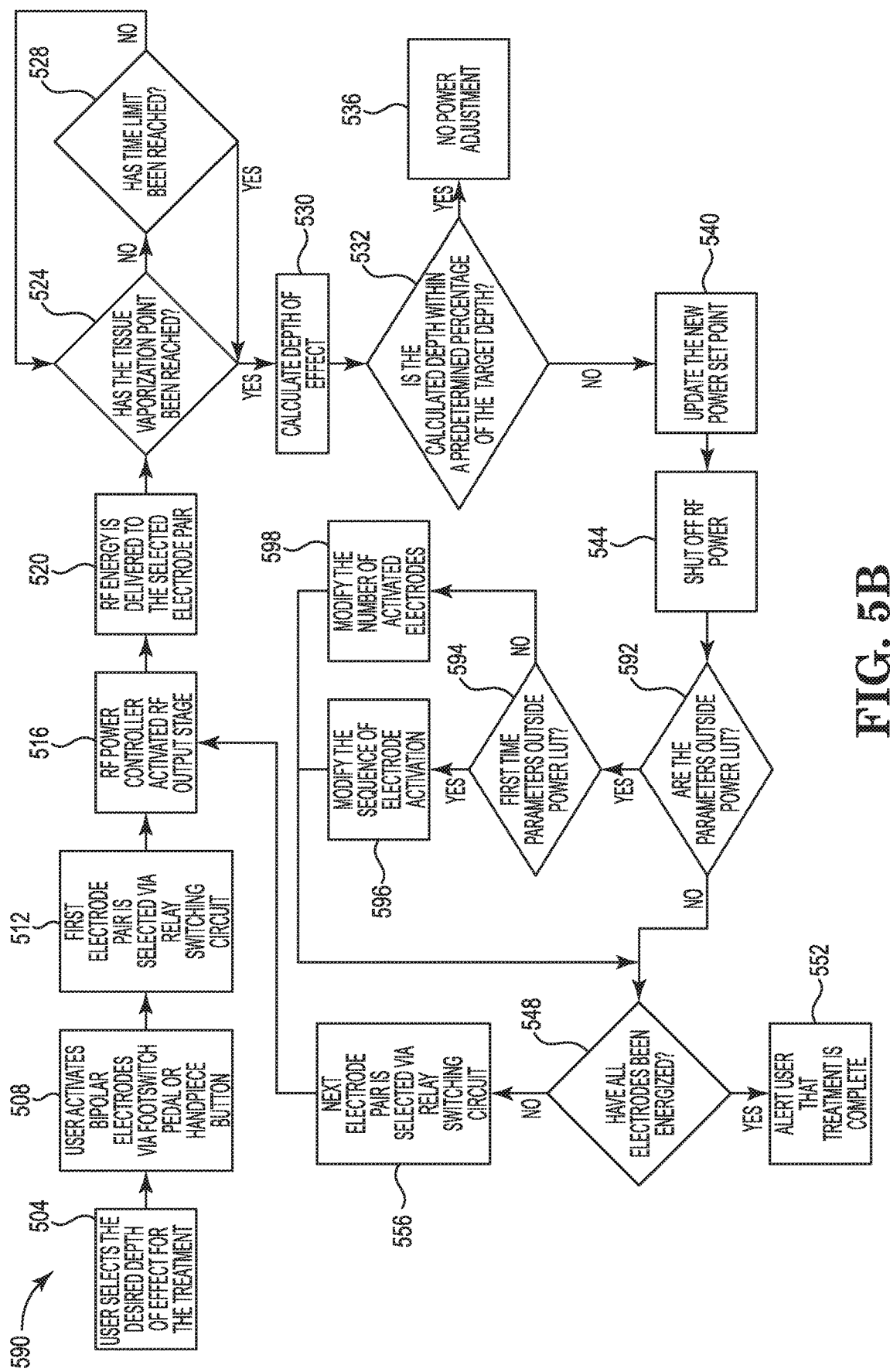

Referring also to FIG. 5B, a flow diagram illustrates a further alternative method of operation 590 of the electrosurgical controller 28, in which like reference numbers with respect to FIG. 5 refer to like elements. FIG. 5B illustrates that modifying the sequence of electrode activation and/or the number of activated electrodes can be performed in conjunction with power level adjustment (as opposed to being performed as an alternative to power level adjustment as illustrated in FIG. 5A). With this arrangement, modifying the sequence of electrode activation and modifying the number of activated electrodes can provide additional attempts to achieve a desired depth of effect in situations where modifying the RF power level cannot accomplish this goal.

In particular, once a new power setting is determined in block 540 for subsequent electrode activations and the RF power is temporarily shut off in block 544, it can be determined in block 592 whether the new power setting determined in block 540 is within the range of power settings contained in the power adjustment look up table 34*b* (FIG. 1). If it is determined that the new power setting is outside of the power look up table power level range, then it can be determined in block 594 whether this is the first time that that the new power setting is outside of the power look up table. If this inquiry is determined in the affirmative and it is the first time that the new power setting is outside of the power look up table, then the sequence of electrode activation can be modified in block 596 in an attempt to thereby achieve the desired depth of effect. Alternatively, if this inquiry is determined in the negative and it is not the first time that the new power setting is outside of the power look up table, then the number of activated electrodes can be modified in block 598.

In block 548, it is determined whether all of the electrodes have been energized. It will be appreciated that when block 596 and/or block 598 is performed (i.e., because the new power set point of block 540 is determined in block 592 to be outside of the power look up table range), the inquiry of block 548 may be changed from a prior iteration of the process. For example, if the sequence of electrode activation is changed from one particular sequence of electrode pair activations to a different particular sequence of electrode pair activations in block 596, then block 548 may use a different electrode listing or table to determine if all electrodes have been energized which may result in some or all electrodes being energized more than once during a procedure.

The example methods 500, 580, 590 set forth in FIGS. 5, 5A, and 5B can be implemented to include a combination of one or more hardware devices and computer programs for controlling a system, such as an electrosurgical system 10 including the RF generator 20 having a processor 26 and memory 22, to perform the example methods to detect vaporization duration during activation of selected electrodes can be used by the controller to determine if a predetermined depth of effect of the RF energy has been reached and system parameters, such as RF power, can be dynamically adjusted accordingly for use in subsequent electrode activations. Methods 500, 580, and 590 can be implemented as a computer readable medium or computer readable device having set of executable instructions in memory 22 for controlling the processor 26 to perform an example method 500, 580, or 590. In one example, computer storage medium, or non-transitory computer readable medium, includes RAM, ROM, EEPROM, flash memory or other memory technology, that can be used to store the desired information and that can be accessed by the electrosurgical system 10 including the RF generator. Accordingly, a propagating signal by itself does not qualify as storage media. Computer readable medium may be located with the RF generator 20 or on a network communicatively connected to the generator 20. Methods 500, 580, and 590 can be applied as computer program, or computer application implemented as a set of instructions stored in the memory 22, and the processor 26 can be configured to execute the instructions to perform a specified task or series of tasks. In one example, the computer program can make use of functions either coded into the program itself or as part of library also stored in the memory 22.

Referring also to FIGS. 6, 6A, and 6B, an example electrosurgical device such as an example catheter assembly 100 of the handpiece 50 includes an expandable tip structure or member, such as a balloon 104 that supports a plurality of attached electrodes 110*a*-110*n* (that may be the same as similar to electrodes 54) for delivering RF energy to a treatment site 52. The catheter assembly 100 includes an elongated body 130 having a proximal end coupled to a handle structure (not shown) that is further coupled to the RF generator 20 via signal lines 38, 42 (FIG. 1) and a distal end to which the balloon 104 is attached. Electrical connections between the electrodes 110*a*-110*n* and the handle structure, and ultimately the RF generator 20, are carried by conductors of an inner catheter assembly within a lumen of the elongated body 130.

Additional features of the handpiece 50, as may be supported by the handle structure, include user actuatable controls such as an on/off control to cause RF energy to be coupled to electrodes 110*a*-110*n*, expansion control with which the balloon 104 can be expanded once brought into contact with the target tissue, and/or fluid delivery control to cause saline to be delivered to the balloon 104.

The inflatable balloon 104 is shown in FIG. 6 in its deflated state or configuration for insertion into and removal from a treatment site 52 (e.g., through a vein, orifice, puncture site, or target tissue under treatment. FIG. 6A shows the balloon 104 in its inflated state or configuration, once deployed to the treatment site, in order to thereby bring the electrodes 110*a*-110*n* into contact with the target tissue. The balloon 104 may be expanded by inflation with a fluid including a liquid or gas into a cavity defined by an inner surface of the balloon. FIG. 6B illustrates use of weeping holes, or apertures 120 to deliver a fluid, such as saline, to the treatment site.

Electrodes 110*a*-110*n* are disposed on an exterior surface of the balloon 104 and may be arranged in bipolar pairs, with each pair including two interleaved electrodes and each electrode of the pair electrically coupled to the relay switching circuit of the RF generator 20 through a respective conductive trace 114*a*-114*n*. As indicated, each electrode of the pair includes a set of spaced-apart traces that are interleaved with a set of spaced-apart trances of the other electrode of the pair. With this bipolar electrode arrangement, one electrode from a pair functions as the active electrode to receive RF current from the RF output stage 30 for delivery to the target tissue (i.e., functions as the first pole of the bipolar pair) and the other electrode of the pair functions as the return electrode to return current to the RF output stage 30 (i.e., functions as the second pole of the bipolar pair). It will be appreciated that a bipolar pair of electrodes could configured at the controller to also act as a single pole.

The size and shape of the balloon 104 can be readily varied to suit a particular surgical procedure and target tissue to be treated, such as a pocket or cavity left behind after a lumpectomy. In the example balloon 104, the electrode pairs (as may be the same as or similar to electrode pairs 58*a*-58*g* of FIG. 2) are arranged in an array comprising rows and columns It will be appreciated however that random spacing of electrodes or electrode pairs is also possible. As an example, each electrode pair may be approximately 10 mm×10 mm in dimension and spaced from an adjacent electrode pair by approximately 5 mm. It will be appreciated that other configurations of electrodes and electrode pairs are possible. The electrode array may be configured to cover a significant portion of the surface area of the balloon 104, as shown.

Also provided on the expandable structure 110 are apertures such as weeping holes 120 through which a fluid, such as saline, can be introduced to the treatment site 52. Weeping holes 120 may have a diameter on the order of 0.005 inches.

Various techniques are possible for providing the balloon 104 and electrodes 110a-110n. For example, the balloon 104 may be comprised of a non-conductive compliant substrate material such as silicone or latex or a non-compliant material such as polyvinyl chloride (PVC), polyethylene (PE), or polyethylene terephthalate (PET). The electrodes 110a-110n may be comprised of a conductive material. For example, the electrodes and/or the balloon can be a biocompatible conductive wire (e.g., stainless steel or titanium) adhered to the exterior surface of the balloon 104 or can be formed of a conductive ink applied (e.g., by a printing or stamping process) to the surface of the balloon substrate material.

Electrodes 110a-110n are exposed to permit contact with the target tissue and the conductive traces 114a-114n may be insulated. Conductive traces 114a-114n may be formed from the same or a different material and process than the electrodes 110a-110n. In an example, the conductive traces 114a-114n may be formed of wire or conductive ink, and/or may include a compliant material and/or may be soldered to the balloon substrate material. Use of a compliant material to form the conductive traces 114a-114n advantageously permits the conductive pathway between the RF generator 20 and the exposed electrodes 110a-110n to be maintained even with expansion and contraction of the balloon 104.

In some embodiments, the balloon material is compliant (for example PVC) in the range of a 50% expansion rate in support of similar expansion rates of the conductive material used to form the electrodes and/or conductive traces. The balloon is compliant because it is not fully inflated. The balloon material may comprise PVC because the conductive material of the traces can adhere to the balloon. It will be appreciated however that other materials for the balloon may be possible. The material thickness of the balloon 104 will be dependent on the size of the weeping holes, balloon pressure, and the manufacturing process surrounding the process of fabricating the holes. The reason for the alignment of these three variables is to control the saline flow rate.

Electrodes 110a-110n can be activated simultaneously or individually, such as in pairs, in a sequence in order to achieve the desired electrosurgical effect. In embodiments in which the electrode pairs are activated in a sequence, the sequence can be predetermined or can be dynamically adjusted based on the vaporization duration. As one example, if the predetermined sequence of electrode activations has electrode pairs being activated in the order in which they are positioned along an axis parallel to the elongated body 130, this predetermined sequence could be adjusted to instead have electrode pairs being activated in the order in which they are positioned radially around the balloon 104.

FIG. 6B illustrates use of the weeping holes 120 to deliver a fluid, such as saline, to the treatment site. Weeping holes 120 can be configured as valves that remain closed when balloon 104 is deflated but which are opened when the balloon 104 is inflated to a given minimum inflation amount and/or internal pressure.

Figure 7:
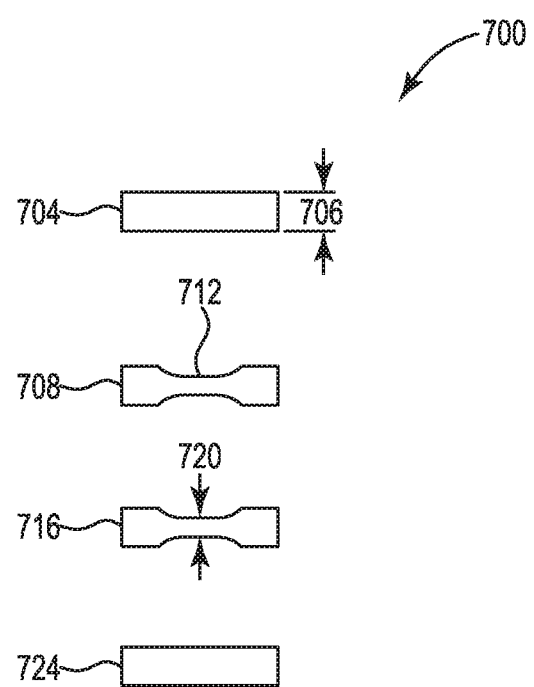
FIG. 7 is a schematic diagram illustrating a portion of the electrosurgical device of FIGS. 6, 6A, and 6B.

Referring also to FIG. 7, an example process 700 for providing the balloon 104 with weeping holes 120 is illustrated. At a process step 704, the balloon material is shown to have a thickness 706. In a step 708, the balloon material is placed under stress to thin an area 712 intended to be provided with a weeping hole. In a step 716, the balloon is cored to form a hole 720 (i.e., a weeping hole) in the stressed, thinned region 712. In step 724, the balloon material is released from the stress and the hole 720 is effectively closed, as shown depending on the application this may or may not be required. In some applications a simple cored hole may surface as the lack of pressure and surface tension will prevent the balloon from unwanted weeping.

Additional details and features of the catheter assembly 100, balloon 104, and weeping holes 120 are described in a co-pending U.S. patent application Ser. No. 13/250,104, filed on Sep. 30, 2011 and entitled Electrosurgical Balloons, which application is hereby incorporated by reference in its entirety.

Saline delivery through weeping holes 120 is one of various options. Alternatively, saline can be dispensed via separate dedicated conduit. Furthermore, while saline has been described as the electrically conductive fluid for filling balloon body 104 and expelling through weeping holes 120, it will be appreciated that other electrically conductive fluids may be used alternatively or additionally and/or the fluid for filling balloon 104 and expelling through weeping holes 120 may also comprise an electrically non-conductive fluid.

It will be appreciated that while a bipolar electrode configuration on a balloon structure 104 is shown, the control methodologies described herein can be used with monopolar electrode configurations or systems employing only a single bipolar electrode pair for electrosurgical treatment. It will also be appreciated that the balloon 104 of FIGS. 6, 6A, and 6B is one of many examples of delivery structures for use with handpieces supporting one or more electrodes for delivery of RF energy to a treatment site. Suitable handpieces need not be expandable or suitable for fluid delivery to benefit from the RF energy control methodologies described herein. For example, a non-balloon expandable member such as that described in U.S. Patent Application Publication No. 2013/0158536, published on Jun. 20, 2013 and entitled Electrosurgical Devices, which application is hereby incorporated by reference in its entirety, or a nitinol-based structure may be used. It will also be appreciated that the RF delivery structure can be any configuration or shape or size suitable for a particular electrosurgical procedure and intended treatment site.

All references cited herein are hereby incorporated herein by reference in their entirety. Having described preferred embodiments, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. An electrosurgical generator, the electrosurgical generator couplable to a plurality of electrodes on an electrosurgical device to deliver a radiofrequency (RF) signal to a target tissue, the electrosurgical generator comprising:

an impedance detector to generate impedance measurements indicative of an impedance associated with the target tissue;

a controller responsive to the impedance measurements from the impedance detector to detect an occurrence of a vaporization point of the target tissue, detect a vaporization duration indicative of a time duration between commencement of delivery of the RF signal and the occurrence of the vaporization point, and determine if a predetermined depth of effect has been reached based at least in part on the vaporization duration;

an RF output stage to generate the RF signal in response to the controller; and a memory storing a plurality of power adjustment values wherein the controller adjusts a power level for the RF signal via the power adjustment values if the predetermined depth of effect has not been reached, wherein each of the power adjustment values is associated with a vaporization duration, a power level of the RF signal, and a difference between a calculated depth of effect and a target depth of effect, wherein the controller applies the power adjustment values to determine a new power level for the RF signal.

2. The electrosurgical generator of claim 1, wherein the controller is configured to detect the occurrence of the vaporization point of the target tissue by detecting an increase in the impedance measurement followed by a plateau in the impedance measurement.

3. The electrosurgical generator of claim 1, comprising a depth of effect look up table having a plurality of depth of effect values, each depth of effect value associated with a vaporization duration and a power level of the RF signal, wherein the controller applies the look up table to determine if the predetermined depth of effect has been reached.

4. The electrosurgical generator of claim 3, wherein each of the plurality of depth of effect values in the depth of effect look up table is further associated with at least one of a distance between activated electrodes and a surface area associated with the plurality of electrodes of the electrosurgical device.

5. The electrosurgical generator of claim 1, wherein the memory includes a power look up table storing the plurality of power adjustment values and wherein the controller applies the power look up table to determine a new power level for the RF signal.

6. The electrosurgical generator of claim 1, wherein each of the plurality power adjustment values is further associated with at least one of a distance between activated electrodes and a surface area associated with the plurality of electrodes.

7. The electrosurgical generator of claim 1, wherein the impedance detector is couplable to the plurality of electrodes and the impedance measurements are indicative of the impedance between the electrodes.

8. An electrosurgical generator, the electrosurgical generator couplable to a plurality of electrodes on an electrosurgical device to deliver a radiofrequency (RF) signal to a target tissue, the electrosurgical generator comprising:

an impedance detector to generate impedance measurements indicative of an impedance associated with the target tissue;

a controller responsive to the impedance measurements from the impedance detector to detect an occurrence of a vaporization point of the target tissue, detect a vaporization duration indicative of a time duration between commencement of delivery of the RF signal and the occurrence of the vaporization point, determine if a predetermined depth of effect has been reached based at least in part on the vaporization duration, and adjust a parameter of the RF signal in the electrosurgical generator during a subsequent activation of an electrode of the plurality of electrodes based at least in part on the vaporization duration, wherein the parameter is associated with activation of the plurality of electrodes;

the controller to adjust the parameter of the RF signal via a predetermined parameter adjustment value if the predetermined depth of effect has not been reached, wherein the predetermined parameter adjustment value is associated with the vaporization duration, a power level of the RF signal, and a difference between a calculated depth of effect and a target depth of effect; and an RF output stage to generate the RF signal in response to the controller.

9. The electrosurgical generator of claim 8 wherein the parameter of the RF signal in the electrosurgical generator comprises a power level of the RF signal, a sequence of activation of the plurality of electrodes, a distance between activated ones of the plurality of electrodes, and a number of activated electrodes.

10. A radiofrequency (RF) electrosurgical system comprising:

a catheter assembly having a plurality of electrodes supported by the catheter assembly and configured to deliver an RF signal to target tissue; and an RF generator comprising:

an impedance detector configured to generate impedance measurements indicative of an impedance associated with the target tissue;

a controller responsive to the impedance measurements from the impedance detector and configured to (a) detect an occurrence of a vaporization point of the target tissue, (b) detect a vaporization duration indicative of a time duration between commencement of delivery of the RF signal and the occurrence of the vaporization point, and (c) determine if a predetermined depth of effect has been reached based at least in part on the vaporization duration a power look up table having a plurality of power adjustment values wherein the controller to adjust a power level via the power look up table for the RF signal if the predetermined depth of effect has not been reached, wherein each of the power adjustment values is associated with a vaporization duration, a power level of the RF signal, and a difference between a calculated depth of effect and a target depth of effect, wherein the controller applies the power adjustment values to determine a new power level for the RF signal; and an RF output stage configured to generate the RF signal in response to the controller.

11. The electrosurgical system of claim 10, wherein the controller is configured to modify a number of activated electrodes if it is determined that the predetermined depth of effect has not been reached.

12. The electrosurgical system of claim 10, wherein the plurality of electrodes comprises a plurality of pairs of electrodes.

13. The electrosurgical system of claim 12, wherein the controller is configured to activate the plurality of pairs of electrodes according to a sequence and to control the sequence of activations of the plurality of electrode pairs based on the vaporization duration.

14. The electrosurgical system of claim 13, wherein the controller is configured to control the sequence of activations of the plurality of electrode pairs by changing a distance between electrodes comprising the electrode pairs.

15. A radiofrequency (RF) electrosurgical system comprising:

a catheter assembly having a plurality of electrodes supported by the catheter assembly and configured to deliver an RF signal to target tissue; and an RF generator comprising:

an impedance detector configured to generate impedance measurements indicative of an impedance associated with the target tissue;

a controller responsive to the impedance measurements from the impedance detector and configured to detect an occurrence of a vaporization point of the target tissue, detect a vaporization duration indicative of a time duration between commencement of delivery of the RF signal and the occurrence of the vaporization point, determine if a predetermined depth of effect has been reached based at least in part on the vaporization duration, and adjust one or more parameters associated with activation of the plurality of electrodes of the electrosurgical system during a subsequent activation of one or more of the plurality of electrodes based at least in part on the vaporization duration;

the controller to adjust the one or more parameters associated with activation of the plurality of electrodes via a predetermined parameter adjustment value stored in a memory device if the predetermined depth of effect has not been reached, wherein the predetermined parameter adjustment value is associated with the vaporization duration, a power level of the RF signal, and a difference between a calculated depth of effect and a target depth of effect; and an RF output stage configured to generate the RF signal in response to the controller.

16. The electrosurgical system of claim 15, wherein the one or more parameters of the electrosurgical system comprise one or more of: a power level of the RF signal, a sequence of activation of the plurality of electrodes, a distance between activated ones of the plurality of electrodes, and a number of activated electrodes.

17. A method of controlling an electrosurgical generator, the electrosurgical generator couplable to a plurality of active electrodes on an electrosurgical device, the method comprising:

for each of the plurality of active electrodes in a succession of selected active electrodes, delivering an amount of radiofrequency (RF) energy to the selected active electrode to reach a vaporization point of tissue;

determining whether a depth of effect of tissue has reached a selected amount; and adjusting the amount of RF energy by a power adjustment value if the depth of effect of tissue has not reached the selected amount the power adjustment value associated with a vaporization duration, a power level of the RF signal, and a difference between a calculated depth of effect and a target depth of effect.

18. The method of claim 17 including adjusting the amount of RF energy for a successive selected active electrode if the depth of effect of tissue has not reached the selected amount.

19. The method of claim 17, wherein the determining whether a depth of effect of tissue has reached includes determining a depth of effect from a look up table in a memory.

20. The method of claim 17 wherein the electrosurgical device includes a corresponding return electrode for each of the plurality of active electrodes.

21. The method of claim 17 wherein the electrosurgical generator includes a plurality of active relays couplable to the active electrodes to deliver the amount of RF energy to the selected active electrode.

22. The method of claim 17 wherein a determination of whether vaporization has occurred includes detecting whether a plateau in a tissue impedance measurement follows a ramp in the impedance measurement has occurred.

23. The method of claim 22 wherein the determination of whether vaporization has occurred is based on tissue impedance measurement samples stored in a memory on the electrosurgical generator.

24. The method of claim 22 wherein delivering the amount of RF energy to the selected active electrode to reach the vaporization point of tissue is based on initial parameters from a look up table.

25. The method of claim 17 wherein a fluid is selectively applied to the tissue.

26. The method of claim 17 including modifying a sequence of active electrodes if the depth of effect of tissue has not reached a selected amount.

27. A method of controlling a radiofrequency (RF) electrosurgical generator, the electrosurgical generator couplable to an electrosurgical device having an electrode in contact with a target tissue, the method comprising:

applying an RF signal to the electrode in contact with the target tissue;

measuring an impedance associated with the target tissue;

analyzing the impedance measurements to determine whether a vaporization point of the target tissue has occurred;

determining a vaporization duration indicative of a time of application of the RF signal to the target tissue prior to the occurrence of the vaporization point; and analyzing the vaporization duration to determine whether a predetermined depth of effect of the RF signal has been reached; and computing a new power level for the RF signal via applying a power adjustment value if the predetermined depth of effect of the RF signal has not been reached, the power adjustment value associated with a vaporization duration, a power level of the RF signal, and a difference between a calculated depth of effect and a target depth of effect.

28. The method of claim 27 wherein analyzing the impedance measurements comprises detecting a plateau in the impedance measurements following a predetermined increase in the impedance measurements.

29. The method of claim 27 wherein analyzing the vaporization duration to determine whether a predetermined depth of effect of the RF signal has been reached comprises using a depth of effect look up table containing a plurality of depth of effect values, each depth of effect value associated with a vaporization duration and a power level of the RF signal.

30. The method of claim 27 wherein computing the new power level comprises applying a power look up table having a plurality of power adjustment values, each power adjustment value associated with a vaporization duration, a power level of the RF signal, and a difference between a calculated depth of effect and a target depth of effect.

31. The method of claim 27 wherein applying an RF signal to an electrode comprises applying the RF signal to a plurality of pairs of electrodes according to a sequence and wherein the method further comprises controlling the sequence based on the vaporization duration.

32. A method for controlling a radiofrequency (RF) electrosurgical generator, the electrosurgical generator couplable to an electrosurgical device having an electrode in contact with a target tissue, the method comprising:

applying an RF signal to the electrode in contact with the target tissue;

measuring an impedance associated with the target tissue;

analyzing the impedance measurements to determine if a vaporization point of the target tissue has occurred;

determining a vaporization duration indicative of a time of application of the RF signal to the target tissue prior to the occurrence of the vaporization point;

determining if a predetermined depth of effect has been reached based at least in part on the vaporization duration; and adjusting a parameter associated with activation of the plurality of electrodes during a subsequent application of the RF signal to an electrode in response to the vaporization duration, the adjusting the parameter via a predetermined parameter adjustment value if the predetermined depth of effect has not been reached, wherein the predetermined parameter adjustment value is associated with the vaporization duration, a power level of the RF signal, and a difference between a calculated depth of effect and a target depth of effect.

33. The method of claim 32 wherein adjusting the parameter comprises adjusting a power level of the RF signal.

34. The method of claim 32 wherein adjusting the parameter comprises modifying a number of activated electrodes.

35. The method of claim 32 wherein applying the RF signal to an electrode comprises applying, in a sequence, the RF signal to selected electrode pairs of a plurality of electrode pairs and wherein adjusting the parameter comprises adjusting the sequence of applying the RF signal to the electrode pairs.

36. The method of claim 32 wherein adjusting the sequence of applying the RF signal to the electrode pairs comprises changing a distance between electrodes of the electrode pairs.

* * * * *